(12) United States Patent
Shinjoh

(10) Patent No.: US 8,771,979 B2
(45) Date of Patent: Jul. 8, 2014

(54) PROCESS FOR PRODUCTION OF BIOMASS FROM A CARBON SOURCE

(75) Inventor: Masako Shinjoh, Kanagawa (JP)

(73) Assignee: DSM IP Assets B.V., Heerlen (NL)

( * ) Notice: Subject to any disclaimer, the term of this patent is extended or adjusted under 35 U.S.C. 154(b) by 494 days.

(21) Appl. No.: 11/991,652

(22) PCT Filed: Sep. 7, 2006

(86) PCT No.: PCT/EP2006/008728
§ 371 (c)(1),
(2), (4) Date: Apr. 18, 2008

(87) PCT Pub. No.: WO2007/028610
PCT Pub. Date: Mar. 15, 2007

(65) Prior Publication Data
US 2009/0123964 A1 May 14, 2009

(30) Foreign Application Priority Data
Sep. 9, 2005 (EP) .................................. 05021390

(51) Int. Cl.
*C12P 1/00* (2006.01)
(52) U.S. Cl.
USPC .......................................................... 435/41
(58) Field of Classification Search
None
See application file for complete search history.

(56) References Cited

U.S. PATENT DOCUMENTS 6,664,082 B1  12/2003  Hoshino et al.

FOREIGN PATENT DOCUMENTS

WO   WO 89/06688   *   7/1989   ................ C12N 9/02

OTHER PUBLICATIONS

GenBank database Acc#YP_192105 24-JAN-2005 from Prust et al, Nat Biotechnol. Feb. 2005;23(2):195-200. Epub Jan. 23, 2005.*
GenBank database Acc#YP 192105 24-JAN-2005 from Prust et al, Nat Biotechnol. Feb. 2005;23(2):195-200. Epub Jan. 23, 2005. Alignment with SEQ ID No. 2.*
Gupta et al, Gluconobacter oxydans: Its Biotechnological Applications. J. Mol. Microbiol. Biotechnol. (2001) 3(3): 445-456.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Sprenger et al, Genetics of pentose-phosphate pathway enzymes of*Escherichia coli* K-12. Archives of Microbiology vol. 164, No. 5 / Nov. 1995.*
Rocha et al, Design and Application of Genome-Scale Reconstructed Metabolic Models From: Methods in Molecular Biology, vol. 416: Microbial Gene Essentiality, pp. 409-431 Edited by: A. L. Osterman and S. Y. Gerdes © Humana Press Inc., Totowa, NJ.*
USPTO in house BLAST alignment SEQ ID No. 1 & 2 vs NCBI #Q5FQ97 from Prust et al, Complete genome sequence of the acetic acid bacterium Gluconobacter oxydans. Nat Biotechnol. Feb. 2005;23(2):195-200. Epub Jan. 23, 2005.*
USPTO in house BLAST alignment SEQ ID No. 12 vs NCBI #CP000009 from Prust et al, Complete genome sequence of the acetic acid bacterium Gluconobacter oxydans. Nat Biotechnol. Feb. 2005;23(2):195-200. Epub Jan. 23, 2005.*
EMBL database Acc# CAA44594.1 from Cleton-Jansen et al, Mol. Gen. Genet. 229 (2), 206-212 (1991). Alignment with SEQ ID No. 11.*
Cleton-Jansen et al., "A single amino acid substitution changes the substrate specificity of quinoprotein glucose dehydrogenase in *Gluconobacter oxydans*" *Mol. Gen. Genetics*, vol. 229, No. 2, pp. 206-212 (1991).
Izu et al., "Purification and characterization of the *Escherichia coli* thermoresistant gluconokinase encoded by the *gntK* gene" *FEBS Lett.*, vol. 394, No. 1, pp. 14-16 (1996).
Prust et al., "Complete genome sequence of the acetic acid bacterium *Gluconobacter oxydans*" *Nature Biotechnol.*, vol. 23, No. 2, pp. 195-200 (Feb. 2005).
Shinjoh et al., "Cloning and Nucleotide sequencing of the membrane-bound L-sorbosone dehydrogenase gene of *Acetobacter liquefaciens* IFO 12258 and its expression in *Gluconobacter oxydans*" *Appl. Environ. Microbiol.*, vol. 61, No. 2, pp. 413-420 (1995).
Int'l Search Report for PCT/EP2006/008728 mailed Mar. 2, 2007.
Written Opinion for PCT/EP2006/008728 mailed Mar. 2, 2007.

* cited by examiner

*Primary Examiner* — Sheridan Swope
(74) *Attorney, Agent, or Firm* — Nixon & Vanderhye P.C.

(57) ABSTRACT

The present invention relates to microorganisms genetically engineered to increase yield and/or efficiency of biomass production from a carbon source, such as e.g. glucose. Also included are processes of using the polynucleotides and modified polynucleotide sequences to transform host microorganisms leading to a microorganism with reduced carbon source diversion, i.e. higher yield and/or efficiency of biomass production from a carbon source such as e.g. glucose.

16 Claims, No Drawings

SEQUENCE LISTING

<160> NUMBER OF SEQ ID NOS: 11

<210> SEQ ID NO 1
<211> LENGTH: 537
<212> TYPE: DNA
<213> ORGANISM: Gluconobacter oxydans DSM 17078

<400> SEQUENCE: 1

```
atgacggaaa atgaaacaca gctgggtctg aagccgcgtt tcctcgtagt catgggcgtg        60
tccgggacag gcaagacgac ggttgcaacc ggactggcca cgcgtctggg ctggcatttt       120
caggaaggcg atgcactgca cccgccggcc aatgtcgaga agatgagcac cggtcagccg       180
ctgaccgatg cggatcgcgc ccctggctt gcgctctgtc atgactggct gcgcgagcag       240
```

```
gtgaaggccg acatggcgc ggtgctgacc tgttccgcgc tcaagcgctc ctatcgtgag    300
cagcttcgcg gtgacgatct gccgatcgag ttcgtgcata tcgacacatc ggccggggaa    360
cttgctgacc gcttgcagcg tcgggaaggg catttcatgc cggcgagcct gctgcccagc    420
cagcttgcga cgcttgaagt gcctggcgac gacgagccgg tgatccgtgt ctcaggcgag    480
aagcatcccg atgtggtgct ggaggagctg atccgccatt ttcaggcgga ggactga      537
```

```
<210> SEQ ID NO 2
<211> LENGTH: 178
<212> TYPE: PRT
<213> ORGANISM: Gluconobacter oxydans DSM 17078

<400> SEQUENCE: 2
```

```
Met Thr Glu Asn Glu Thr Gln Leu Gly Leu Lys Pro Arg Phe Leu Val
1               5                   10                  15

Val Met Gly Val Ser Gly Thr Gly Lys Thr Thr Val Ala Thr Gly Leu
            20                  25                  30

Ala Thr Arg Leu Gly Trp His Phe Gln Glu Gly Asp Ala Leu His Pro
        35                  40                  45

Pro Ala Asn Val Glu Lys Met Ser Thr Gly Gln Pro Leu Thr Asp Ala
    50                  55                  60

Asp Arg Ala Pro Trp Leu Ala Leu Cys His Asp Trp Leu Arg Glu Gln
65                  70                  75                  80

Val Lys Ala Gly His Gly Ala Val Leu Thr Cys Ser Ala Leu Lys Arg
                85                  90                  95

Ser Tyr Arg Glu Gln Leu Arg Gly Asp Asp Leu Pro Ile Glu Phe Val
            100                 105                 110

His Ile Asp Thr Ser Ala Gly Glu Leu Ala Asp Arg Leu Gln Arg Arg
        115                 120                 125

Glu Gly His Phe Met Pro Ala Ser Leu Leu Pro Ser Gln Leu Ala Thr
    130                 135                 140

Leu Glu Val Pro Gly Asp Asp Glu Pro Val Ile Arg Val Ser Gly Glu
145                 150                 155                 160

Lys His Pro Asp Val Val Leu Glu Glu Leu Ile Arg His Phe Gln Ala
                165                 170                 175

Glu Asp
```

```
<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgacggaaa atgaaacaca                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tcagtcctcc gcctgaaaat                                                 20

<210> SEQ ID NO 5
```

```
<211> LENGTH: 26
<212> TYPE: DNA
<213> ORGANISM: Artificial Sequence
<220> FEATURE:
<223> OTHER INFORMATION: primer

<400> SEQUENCE: 5
cgacccggta gatctcatcc ttgacc                                          26

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
ggacggtgtg gagcctcgag agccatgaag atg                                  33

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gcacggccgg gcatgccact tgtggc                                          26

<210> SEQ ID NO 8
<211> LENGTH: 46
<212> TYPE: DNA
<213> ORGANISM: Artificial Sequence
<220> FEATURE:
<223> OTHER INFORMATION: primer

<400> SEQUENCE: 8
cccatccact aaacttaaac acgtgccgcc gatctggcgg gagacg                    46

<210> SEQ ID NO 9
<211> LENGTH: 49
<212> TYPE: DNA
<213> ORGANISM: Artificial Sequence
<220> FEATURE:
<223> OTHER INFORMATION: primer

<400> SEQUENCE: 9
tgtttaagtt tagtggatgg gctctccacg gctggcaacc tcggcttcc                 49

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
ccggttgtga ggcggtcgac tggcagtcgg tgg                                  33

<210> SEQ ID NO 11
<211> LENGTH: 2427
<212> TYPE: DNA
<213> ORGANISM: Gluconobacter oxydans DSM 17078

<400> SEQUENCE: 11
atgagcacaa catcccggcc agggctctgg gccctgatta cggccgcggt attcgcgctt    60
```

```
tgcggcgcga tccttaccgt tggcggcgca tgggtcgctg ccatcggcgg ccctctctat    120
tatgtcatcc ttggcctggc acttctcgcc acggctttcc tctcattccg gcgcaacccg    180
gctgccctct acctgttcgc agtcgtcgtc ttcggaacgg tcatctggga actcaccatt    240
gtcggtctcg acatctgggc cctgatcccg cgctcggaca tcgtcatcat cctcggcatc    300
tggctgctgc tgccgttcgt ctcccgccag atcggcggca cgcggacgac cgtcctgccg    360
ctcgccggcg ccgttggcgt tgcggttctg gccctgttcg ccagcctctt caccgacccg    420
catgacatca gcggcgaact gccgacgcag atcgcaaacg cctcccccgc cgacccggac    480
aacgtcccgg ccagcgaatg gcacgcttat ggtcgtacgc aggccggtga ccgctggtcc    540
ccgctgaacc agatcaacgc gtccaacgtc agcaacctca aggtcgcatg gcatatccac    600
accaaggata tgatgaactc caacgacccg ggcgaagcga cgaacgaagc gaccccgatc    660
gagttcaaca acacgcttta tatgtgctcg ctgcaccaga agctgtttgc ggttgatggt    720
gccaccggta acgtcaagtg ggtctacgat ccgaagctcc agatcaaccc tggcttccag    780
catctgacct gccgtggcgt cagcttccac gaaacgccgg ccaatgccac ggattccgat    840
ggcaatcccg ctccgacgga ctgcgccaag cgcatcatcc tgccggtcaa tgatggccgt    900
ctggttgaag tcgatgccga cacgggcaag acctgctccg gcttcggcaa caatggcgag    960
atcgatctgc gcgttccgaa ccagcccta  cgacgcccg  ccagtatga  gccgacgtcc   1020 ccgccggtca tcacggacaa gctgatcatc gccaacagcg ccatcaccga taacggttcg   1080
gtcaagcagg cttcgggcgc cacgcaggca ttcgacgtct acaccggcaa gcgcgtctgg   1140
gtgttcgatg cgtccaaccc ggatccgaac cagcttccgg atgacagcca ccctgtcttc   1200
cacccgaact ccccgaactc ctggatcgtg tcgtcctacg acaggaatct gaacctcgtg   1260
tacatcccga tgggcgtggg tactcccgac cagtggggcg gtgaccgcac gaaggattcc   1320
gagcgtttcg ctccgggtat cgtcgcgctg aacgccgata cgggcaagct cgcctggttc   1380
taccagaccg ttcatcacga tctgtgggac atggacgttc cgtcccagcc gagccttgtg   1440
gacgtaacgc agaaggacgg cacgcttgtt ccggccatct acgctccgac caagaccggc   1500
gacatcttcg tcctcgaccg tcgtaccggc aaggaaatcg tcccggctcc ggaaaccccg   1560
gttccccagg gcgccgctcc gggcgatcac accagcccga cccagccgat gtcgcagctg   1620
accctgcgtc cgaagaaccc gctgaacgac tccgatatct ggggcggcac gatcttcgac   1680
cagatgttct gcagcatcta tttccacaga ctgcgctacg aaggcccctt cacgccgccg   1740
tcgctcaagg gttcgctcat cttccgggc  gatctgggaa tgttcgaatg gggcggtctg   1800
gccgtcgatc cgcagcgtca ggtggctttc gccaacccga tctccctgcc gttcgtctcc   1860
cagcttgttc cccgtggacc gggcaacccg ctctggcctg aaaaggacgc caagggcacg   1920
ggtggtgaaa ccggcctgca gcacaactat ggcattccgt atgccgtcaa cctgcatccg   1980
ttcctggatc cggtgctgct gccgttcggc atcaagatgc cgtgccgcac gccgccctgg   2040
ggctatgtcg ccggtattga cctgaagacc aacaaggtcg tctggcagca ccgcaacggc   2100
accctgcgtg actccatgta tggcagctcc ctgccgatcc cgctgccgcc gatcaagatc   2160
ggtgtcccga gctcggtgg  cccgctctcc acggctggca acctcggctt cctgacggcg   2220
tccatggatt actacatccg tgcgtacaac ctgacgacgg gcaaagtgct gtggcaggac   2280
cgcctgccgg ctggtgccca ggcaacgccg atcacctatg cgatcaacgg caagcagtac   2340
```

```
atcgtaacct atgcaggcgg acacaactcg ttcccgaccc gcatgggcga cgacatcatc    2400
gcctacgccc tgcccgatca gaaatga                                        2427
```

PROCESS FOR PRODUCTION OF BIOMASS FROM A CARBON SOURCE

This application is the U.S. national phase under 35 USC 371 of Int'l Application No. PCT/EP2006/008728, filed 7 Sep. 2006, which designated the U.S. and claims priority to European Patent Application No. 05021390.9, filed 9 Sep. 2005; the entire contents of each of which are hereby incorporated by reference.

The present invention relates to microorganisms genetically engineered to increase yield and/or efficiency of biomass production from a carbon source, such as e.g. glucose. Processes for generating such microorganisms are also provided by the present invention. The invention also relates to polynucleotide sequences comprising genes that encode proteins that are involved in the bioconversion of a carbon source such as e.g. glucose into biomass. The invention also features polynucleotides comprising the full-length polynucleotide sequences of the novel genes and fragments thereof, the novel polypeptides encoded by the polynucleotides and fragments thereof, as well as their functional equivalents. Also included are processes of using the polynucleotides and modified polynucleotide sequences to transform host microorganisms leading to a microorganism with reduced carbon source diversion, i.e. higher yield and/or efficiency of biomass production from a carbon source such as e.g. glucose.

The bioconversion of a carbon source may involve many different metabolic routes, and involve several enzymatic steps to generate biomass, wherein the enzymes may be located in the cytosol, on the membrane or in the periplasmic space of a host cell. Furthermore, transporters may also play an important role in the efficient conversion of a carbon source into biomass.

For instance, in the case of acetic acid bacteria, which are obligate aerobe, gram-negative microorganisms belonging to the genus *Acetobacter, Gluconobacter*, and *Gluconacetobacter*, these microorganisms are able to oxidize D-glucose at the periplasmic membrane level to D-gluconate by means of a membrane-bound D-glucose dehydrogenase, and transport D-gluconate into the cytosol. D-gluconate can then be phosphorylated by gluconokinase to D-gluconate-6-phosphate. In addition to that, it is believed that D-glucose can be directly transported into the cytosol and then converted into D-gluconate by means of a cytosolic NAD(P)-dependent D-glucose dehydrogenase. Furthermore, D-glucose transported into the cytosol can also be first phosphorylated to D-glucose-6-phosphate by glucokinase and then be dehydrogenated to D-gluconate-6-phosphate. D-gluconate-6-phosphate may enter the pentose phosphate pathway, being further metabolized to produce reducing power in the form of NAD(P)H and tricarboxylic compounds necessary for growth and maintenance.

Proteins, in particular enzymes, that are active in the metabolization of glucose are herein referred to as being involved in the Glucose Metabolization System. Such proteins are abbreviated herein as GMS proteins and function in the direct metabolization or bioconversion of a carbon source such as e.g. glucose into biomass.

One disadvantage of such bioconversion processes, however, is the diversion of carbon sources or intermediates throughout said bioconversion process such that for instance the next (enzymatic) step cannot be performed in an optimal way, leading to the loss of available carbon substrate material for conversion into biomass and resultant energy losses, in form of e.g. ATP or NADPH. In the case of for instance the bioconversion of glucose into biomass, this loss may be due to transporting the glucose or an intermediate thereof out of the cytosol or by using the glucose or the resulting intermediates as substrates for other pathways not leading to the production of biomass.

It is an object of the present invention to provide microorganisms which are engineered in such a way that the carbon source diversion throughout the bioconversion of carbon sources, such as e.g. glucose, is altered, e.g. via reduction of carbon source diversion, leading to higher production and/or yield of biomass produced from such carbon sources.

Surprisingly, it has now been found that GMS proteins or subunits of such proteins having activity towards or which are involved in the bioconversion of a carbon source such as e.g. glucose play an important role in the production of biomass.

In one embodiment, GMS proteins of the present invention are selected from oxidoreductases [EC 1], preferably oxidoreductases acting on the CH—OH group of donors [EC 1.1], more preferably oxidoreductases with $NAD^+$ or $NADP^+$ as acceptor [EC 1.1.1] and oxidoreductases with a quinone or similar compound as acceptor [EC 1.1.5], most preferably NADP-glucose dehydrogenase [EC 1.1.1.47] and PQQ dependent glucose dehydrogenase [EC 1.1.5.2] or from transferases [EC 2], preferably transferases transferring phosphorus-containing groups [EC 2.7], more preferably phosphotransferases with an alcohol group as acceptor [EC 2.7.1], most preferably gluconokinase [EC 2.7.1.12].

Furthermore, the GMS proteins or subunits of such proteins having activity towards or which are involved in the bioconversion of a carbon source such as e.g. glucose into biomass are selected from the group consisting of membrane-bound PQQ-dependent D-glucose dehydrogenase, NAD(P)-dependent D-glucose dehydrogenase, cytosolic D-glucose kinase, enzymes or enzyme subunits having activity towards or involved in the assimilation of D-gluconate such as membrane-bound FAD-dependent D-gluconate dehydrogenase (2-keto-D-gluconate-forming), membrane-bound PQQ-dependent D-gluconate dehydrogenase (5-keto-D-gluconate-forming), cytosolic D-gluconate kinase, enzymes or enzyme subunits having activity towards or involved in the assimilation of 2 KD such as membrane-bound FAD-dependent 2-keto-D-gluconate dehydrogenase, NAD(P)-dependent glucose-1-dehydrogenase, flavin containing gluconate-2-dehydrogenase, gluconate-5-dehydrogenase (5-keto-D-gluconate reductase), and cytosolic NAD(P)-dependent 2-keto-D-gluconate reductase.

In particular, it has now been found that GMS proteins encoded by polynucleotides having a nucleotide sequence that hybridizes preferably under highly stringent conditions to a sequence shown in SEQ ID NO:1 play an important role in the bioconversion of a carbon source such as e.g. glucose to biomass. It has also been found, that by genetically altering such nucleotides in a microorganism, such as for example *Gluconobacter*, the efficiency of said bioconversion within said microorganism can be even greatly improved leading e.g. to higher production and/or yield of biomass from a carbon source such as e.g. glucose.

Consequently, the invention relates to a polynucleotide selected from the group consisting of:
(a) polynucleotides encoding a polypeptide comprising the amino acid sequence according to SEQ ID NO:2;
(b) polynucleotides comprising the nucleotide sequence according to SEQ ID NO:1;
(c) polynucleotides comprising a nucleotide sequence obtainable by nucleic acid amplification such as polymerase chain reaction, using genomic DNA from a microorganism as a template and a primer set according to SEQ ID NO:3 and SEQ ID NO:4;

(d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the activity of a transferase [EC 2], preferably transferase transferring phosphorus-containing groups [EC 2.7] (GMS 08);

(e) polynucleotides the complementary strand of which hybridizes under stringent conditions to a polynucleotide as defined in any one of (a) to (d) and which encode a transferase [EC 2], preferably transferase transferring phosphorus-containing groups [EC 2.7] (GMS 08); and (f) polynucleotides which are at least 70%, such as 85, 90 or 95% homologous to a polynucleotide as defined in any one of (a) to (d) and which encode a transferase [EC 2], preferably transferase transferring phosphorus-containing groups [EC 2.7] (GMS 08);

or the complementary strand of such a polynucleotide.

The GMS protein as isolated from *Gluconobacter oxydans* DSM 17078 shown in SEQ ID NO:2 and described herein was found to be a particularly useful GMS protein, since it appeared that it performs a crucial function in the bioconversion of a carbon source such as e.g. glucose to biomass in microorganisms, in particular in bacteria, such as acetic acid bacteria, such as *Gluconobacter, Acetobacter* and *Gluconacetobacter*. Accordingly, the invention relates to a polynucleotide encoding a polypeptide according to SEQ ID NO:2. This protein may be encoded by a nucleotide sequence as shown in SEQ ID NO:1. The invention therefore also relates to polynucleotides comprising the nucleotide sequence according to SEQ ID NO:1.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). From the searches, the GMS 08 polynucleotide according to SEQ ID NO:1 was annotated as encoding a protein having gluconate kinase activity.

A nucleic acid according to the invention may be obtained by nucleic acid amplification using cDNA, mRNA or alternatively, genomic DNA, as a template and appropriate oligonucleotide primers such as the nucleotide primers according to SEQ ID NO:3 and SEQ ID NO:4 according to standard PCR amplification techniques. The nucleic acid thus amplified may be cloned into an appropriate vector and characterized by DNA sequence analysis.

The template for the reaction may be cDNA obtained by reverse transcription of mRNA prepared from strains known or suspected to comprise a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

Accordingly, the invention relates to polynucleotides comprising a nucleotide sequence obtainable by nucleic acid amplification such as polymerase chain reaction, using DNA such as genomic DNA from a microorganism as a template and a primer set according to SEQ ID NO:3 and SEQ ID NO:4.

The invention also relates to polynucleotides comprising a nucleotide sequence encoding a fragment or derivative of a polypeptide encoded by a polynucleotide as described herein wherein in said derivative one or more amino acid residues are conservatively substituted compared to said polypeptide, and said fragment or derivative has the activity of a GMS polypeptide, preferably a GMS 08 polypeptide.

The invention also relates to polynucleotides the complementary strand of which hybridizes under stringent conditions to a polynucleotide as defined herein and which encode a GMS polypeptide, preferably a GMS 08 polypeptide.

The invention also relates to polynucleotides which are at least 70% identical to a polynucleotide as defined herein and which encode a GMS polypeptide; and the invention also relates to polynucleotides being the complementary strand of a polynucleotide as defined herein above.

The invention also relates to primers, probes and fragments that may be used to amplify or detect a DNA according to the invention and to identify related species or families of microorganisms also carrying such genes.

The present invention also relates to vectors which include polynucleotides of the invention and microorganisms which are genetically engineered with the polynucleotides or said vectors.

The invention also relates to processes for producing microorganisms capable of expressing a polypeptide encoded by the above defined polynucleotide and a polypeptide encoded by a polynucleotide as defined above.

The invention also relates to microorganisms wherein the activity of a GMS polypeptide, preferably a GMS 08 polypeptide, is enhanced and/or improved so that the yield and/or production of biomass which is produced through bioconversion of a carbon source such as e.g. glucose is increased.

A suitable carbon source that can be converted into biomass may be for instance glucose or selected from carbon sources the assimilation of which results in the formation of glucose, in particular D-glucose, such as sucrose, maltose, starch, cellulose, cellobiose, lactose, isomaltose, dextran, trehalose or mixtures thereof.

The skilled person will know how to enhance and/or improve the activity of a GMS protein, preferably a GMS 08 protein. Such may be for instance accomplished by either genetically modifying the host organism in such a way that it produces more or more stable copies of the GMS protein, preferably the GMS 08 protein, than the wild type organism or by increasing the specific activity of the GMS protein, preferably the GMS 08 protein.

In the following description, procedures are detailed to achieve this goal, i.e. the increase in the yield and/or production of biomass which is produced through bioconversion of a carbon source such as e.g. glucose by increasing the activity of a GMS 08 protein. These procedures apply mutatis mutandis for other GMS proteins.

Modifications in order to have the organism produce more copies of the GMS 08 gene and/or protein may include the use of a strong promoter, or the mutation (e.g. insertion, deletion or point mutation) of (parts of) the GMS 08 gene or its regulatory elements. It may also involve the insertion of multiple copies of the gene into a suitable microorganism. An increase in the specific activity of a GMS 08 protein may also be accomplished by methods known in the art. Such methods may include the mutation (e.g. insertion, deletion or point mutation) of (parts of) the GMS 08 gene. A gene is said to be "overexpressed" if the level of transcription of said gene is enhanced in comparison to the wild type gene. This may be measured by for instance Northern blot analysis quantifying the amount of mRNA as an indication for gene expression. As used herein, a gene is overexpressed if the amount of generated mRNA is increased by at least 1%, 2%, 5% 10%, 25%, 50%, 75%, 100%, 200% or even more than 500%, compared to the amount of mRNA generated from a wild-type gene.

Also known in the art are methods of increasing the activity of a given protein by contacting the GMS 08 protein with specific enhancers or other substances that specifically interact with the GMS 08 protein. In order to identify such specific enhancers, the GMS 08 protein may be expressed and tested for activity in the presence of compounds suspected to enhance the activity of the GMS 08 protein. The activity of the GMS 08 protein may also be increased by stabilizing the messenger RNA encoding GMS 08. Such methods are also known in the art, see for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

The invention may be performed in any microorganism carrying a GMS 08 gene or equivalent or homologue thereof. Suitable microorganisms may be selected from the group consisting of yeast, algae and bacteria, either as wild type strains, mutant strains derived by classic mutagenesis and selection methods or as recombinant strains. Examples of such yeast may be, e.g., *Candida, Saccharomyces, Zygosaccharomyces, Schizosaccharomyces,* or *Kluyveromyces*. An example of such algae may be, e.g., *Chlorella*. Examples of such bacteria may be, e.g., *Gluconobacter, Acetobacter, Gluconacetobacter, Ketogulonicigenium, Pantoea, Pseudomonas,* such as, e.g., *Pseudomonas putida,* and *Escherichia,* such as, e.g., *Escherichia coli*. Preferred are *Gluconobacter* or *Acetobacter aceti*, such as for instance *G. oxydans, G. cerinus, G. frateurii, A. aceti* subsp. *xylinum* or *A. aceti* subsp. *orleanus*, preferably *G. oxydans* DSM 17078. *Gluconobacter oxydans* DSM 17078 (formerly known as *Gluconobacter oxydans* N44-1) has been deposited at Deutsche Sammlung von Mikroorganismen und Zellkulturen (DSMZ), Mascheroder Weg 1B, D-38124 Braunschweig, Germany according to the Budapest Treaty on 26. Jan. 2005.

Microorganisms which can be used for the present invention may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Jusohonmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateurii* (formerly known as *G. industrius*) IFO 3260, *Gluconobacter cerinus* IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N 44-1 as another example of a preferred bacterium is a derivative of the strain IFO 3293 and is described in Sugisawa et al., Agric. Biol. Chem. 54: 1201-1209, 1990.

A microorganism as of the present invention may carry further modifications either on the DNA or protein level (see above), as long as such modification(s) has/have a direct impact on the yield, production and/or efficiency of biomass from a substrate such as e.g. glucose. Such further modifications may for instance affect other genes encoding oxidoreductases or isomerases as described above, in particular genes encoding NAD(P)-glucose dehydrogenase, PQQ-dependent glucose dehydrogenase, FAD-dependent gluconate-2-dehydrogenase, NAD(P)-gluconate-2-dehydrognease, gluconate-5-dehydrogenase, 2-ketogluconate dehydrogenase, 2,5-di-ketogluconate dehydrogenase, gluconate oxidase, phosphoglucoseisomerase, or further genes encoding enzymes involved in the pentose phosphate pathway, such as for instance 6-phosphogluconate dehydrogenase, 6-phosphogluconolactonase, ribulose-5-phosphate 3-epimerase, transaldolase or transketolase, or further genes encoding enzymes linking the pentose phosphate pathway to other pathways of carbon metabolism, such as for instance 6-phosphogluconate dehydratase, fructose-1,6-bisphosphate or phosphofructokinase. In one particular embodiment, such further modification may affect the gene coding for membrane-bound PQQ-dependent glucose dehydrogenase activity, wherein the activity of such gene is reduced or nullified.

A preferred gene coding for such membrane-bound PQQ-dependent glucose dehydrogenase is shown in SEQ ID NO:11 or a gene which is at least 70, 80, 90, or 98% identical. Methods of performing such modifications are known in the art, with some examples further described herein.

In accordance with a further object of the present invention there is provided the use of a polynucleotide as defined above or a microorganism which is genetically engineered using such polynucleotides in the efficient production of biomass from a carbon source.

The invention also relates to processes for the expression of endogenous genes in a microorganism, to processes for the production of polypeptides as defined above in a microorganism and to processes for the production of microorganisms capable of growth on a given carbon source such as e.g. glucose. All these processes comprise the step of altering a microorganism, wherein "altering" as used herein encompasses the process for "genetically altering" or "altering the composition of the cell culture media and/or methods used for culturing" in such a way that the yield and/or productivity of biomass can be improved compared to the wild-type organism. As used herein, "improved yield of biomass" means an increase of at least 5%, 10%, 25%, 30%, 40%, 50%, 75%, 100%, 200% or even more than 500%, depending on the carbon source used for growth, compared to a wild-type microorganism, i.e. a microorganism which is not genetically altered.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

Advantageous embodiments of the invention become evident from the dependent claims. These and other aspects and embodiments of the present invention should now be apparent to those skilled in the art based on the teachings herein.

The sequence of the gene comprising a nucleotide sequence according to SEQ ID NO:1 encoding a GMS 08 protein was determined by sequencing a genomic clone obtained from *Gluconobacter oxydans* DSM 17078.

The invention also relates to a polynucleotide encoding at least a biologically active fragment or derivative of a GMS 08 polypeptide as shown in SEQ ID NO:2.

As used herein, "biologically active fragment or derivative" means a polypeptide which retains essentially the same biological function or activity as the polypeptide shown in SEQ ID NO:2. Examples of biological activity may for instance be enzymatic activity, signaling activity or antibody reactivity activity. The term "biological function" or "functional equivalent" as used herein means that the protein has essentially the same biological activity, e.g. enzymatic, signaling or antibody reactivity activity, as a polypeptide shown in SEQ ID NO:2.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide", "gene" and "recombinant gene" refer to nucleic acid molecules which may be isolated from chromosomal DNA, which include an open reading frame encoding a protein, e.g. *G. oxydans* DSM 17078 GMS proteins. A polynucleotide may include a polynucleotide sequence as shown in SEQ ID NO:1 or fragments thereof and regions upstream and downstream of the gene sequences which may include, for example, promoter regions, regulator regions and terminator regions important for the appropriate expression and stabilization of the polypeptide derived thereof.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of GMS proteins may exist within a population, e.g., the *Gluconobacter oxydans* population. Such genetic polymorphism in the GMS 08 gene may exist among individuals within a population due to natural variation or in cells from different populations. Such natural variations can typically result in 1-5% variance in the nucleotide sequence of the GMS 08 gene. Any and all such nucleotide variations and the resulting amino acid polymorphism in GMS 08 are the result of natural variation and that do not alter the function or biological activity of GMS proteins are intended to be within the scope of the invention.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

The sequence information as provided herein should not be so narrowly construed as to require inclusion of erroneously identified bases. The specific sequences disclosed herein may be readily used to isolate the complete gene from a microorganism capable of converting a given carbon source such as e.g. glucose into biomass, in particular *Gluconobacter oxydans*, preferably *Gluconobacter oxydans* DSM 17078 which in turn may easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequence shown in SEQ ID NO:1, for example a fragment which may be used as a probe or primer such as for instance SEQ ID NO:3 or SEQ ID NO:4 or a fragment encoding a portion of a protein according to the invention. The nucleotide sequence determined from the cloning of the GMS 08 gene allows for the generation of probes and primers designed for use in identifying and/or cloning other GMS 08 family members, as well as GMS 08 homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence shown in SEQ ID NO:1 or a fragment or derivative thereof.

A nucleic acid molecule encompassing all or a portion of the nucleic acid sequence of SEQ ID NO:1 may be isolated by the polymerase chain reaction (PCR) using synthetic oligonucleotide primers designed based upon the sequence information contained herein.

A nucleic acid of the invention may be amplified using cDNA, mRNA or alternatively, genomic DNA, as a template and appropriate oligonucleotide primers according to standard PCR amplification techniques. The nucleic acid thus amplified may be cloned into an appropriate vector and characterized by DNA sequence analysis.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, may be used as hybridization probes or polymerase chain reaction (PCR) primers. Uses of the nucleic acid molecules of the present invention that do not encode a polypeptide having a GMS 08 activity include, inter alia, (1) isolating the gene encoding the protein of the present invention, or allelic variants thereof from a cDNA library, e.g., from other organisms than *Gluconobacter oxydans* and (2) Northern blot analysis for detecting expression of mRNA of said protein in specific cells or (3) use in abolishing or altering the function or activity of homologous GMS 08 genes in said other organisms.

Probes based on the nucleotide sequences provided herein may be used to detect transcripts or genomic sequences encoding the same or homologous proteins for instance in other organisms. Nucleic acid molecules corresponding to natural variants and non-*G. oxydans* homologues of the *G. oxydans* GMS 08 DNA of the invention which are also embraced by the present invention may be isolated based on their homology to the *G. oxydans* GMS 08 nucleic acid disclosed herein using the *G. oxydans* DNA, or a portion thereof, as a hybridization probe according to standard hybridization techniques, preferably under highly stringent hybridization conditions.

In preferred embodiments, the probe further comprises a label group attached thereto, e.g., the label group can be a radioisotope, a fluorescent compound, an enzyme, or an enzyme cofactor.

Homologous gene sequences may be isolated, for example, by performing PCR using two degenerate oligonucleotide primer pools designed on the basis of nucleotide sequences as taught herein.

The template for the reaction may be cDNA obtained by reverse transcription of mRNA prepared from strains known or suspected to express a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

PCR technology can also be used to isolate full-length cDNA sequences from other organisms. For example, RNA may be isolated, following standard procedures, from an appropriate cellular or tissue source. A reverse transcription reaction may be performed on the RNA using an oligonucleotide primer specific for the most 5'-end of the amplified fragment for the priming of first strand synthesis.

The resulting RNA/DNA hybrid may then be "tailed" (e.g., with guanines) using a standard terminal transferase reaction, the hybrid may be digested with RNaseH, and second strand synthesis may then be primed (e.g., with a poly-C primer). Thus, cDNA sequences upstream of the amplified fragment may easily be isolated. For a review of useful cloning strategies, see e.g., Sambrook et al., supra; and Ausubel et al., supra.

Also, nucleic acids encoding other GMS 08 family members, which thus have a nucleotide sequence that differs from a nucleotide sequence according to SEQ ID NO:1, are within the scope of the invention. Moreover, nucleic acids encoding GMS 08 proteins from different species which thus may have a nucleotide sequence which differs from a nucleotide sequence shown in SEQ ID NO:1 are within the scope of the invention.

The invention also relates to an isolated polynucleotide hybridisable under stringent conditions, preferably under highly stringent conditions, to a polynucleotide according to the present invention, such as for instance a polynucleotide shown in SEQ ID NO:1. Advantageously, such polynucleotide may be obtained from a microorganism capable of converting a given carbon source such as e.g. glucose into biomass, in particular *Gluconobacter oxydans*, preferably *Gluconobacter oxydans* DSM 17078.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO:1 or the complement thereof.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Preferably, an isolated nucleic acid molecule of the invention that hybridizes under preferably highly stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *G. oxydans* GMS 08 protein.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, genomic DNA or cDNA libraries constructed from other organisms, e.g. microorganisms capable of converting of a given carbon source such as e.g. glucose into biomass, in particular other *Gluconobacter* species may be screened.

For example, *Gluconobacter* strains may be screened for homologous polynucleotides by Northern blot analysis. Upon detection of transcripts homologous to polynucleotides according to the invention, DNA libraries may be constructed from RNA isolated from the appropriate strain, utilizing standard techniques well known to those of skill in the art. Alternatively, a total genomic DNA library may be screened using a probe hybridisable to a polynucleotide according to the invention.

A nucleic acid molecule of the present invention, such as for instance a nucleic acid molecule shown in SEQ ID NO:1 or a fragment or derivative thereof, may be isolated using standard molecular biology techniques and the sequence information provided herein. For example, using all or portion of the nucleic acid sequence shown in SEQ ID NO:1 as a hybridization probe, nucleic acid molecules according to the invention may be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at URL accelrys[dot]com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at URL accelrys[dot]com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available at URL vega[dot]igh[dot]cnrs[dot]fr [slash]bin[slash]align-guess[dot]cgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. See URL ncbi[dot]nlm[dot]nih[dot] gov.

In another preferred embodiment, an isolated nucleic acid molecule of the invention comprises a nucleic acid molecule which is the complement of a nucleotide sequence as of the present invention, such as for instance the sequence shown in SEQ ID NO:1. A nucleic acid molecule, which is complementary to a nucleotide sequence disclosed herein, is one that is sufficiently complementary to a nucleotide sequence shown in SEQ ID NO:1 such that it may hybridize to said nucleotide sequence thereby forming a stable duplex.

In a further preferred embodiment, a nucleic acid of the invention as shown in SEQ ID NO:1 or the complement thereof contains at least one mutation leading to a gene product with modified function/activity. The at least one mutation may be introduced by methods described herein. In one aspect, the at least one mutation leads to a GMS 08 protein whose function and/or activity compared to the wild type counterpart is enhanced or improved. Methods for introducing such mutations are well known in the art.

The term "increase" of activity as used herein encompasses increasing activity of one or more polypeptides in the producing organism, which in turn are encoded by the corresponding polynucleotides described herein. There are a number of methods available in the art to accomplish increase of activity of a given protein, in this case the GMS 08 protein. In general, the specific activity of a protein may be increased or the copy number of the protein may be increased. The term increase of activity or equivalent expressions also encompasses the situation wherein GMS 08 protein activity is introduced in a cell that did not contain this activity before, e.g. by introducing a gene encoding GMS 08 in a cell that did not contain an equivalent of this gene before, or that could not express an active form of the corresponding protein before.

To facilitate such an increase, the copy number of the genes corresponding to the polynucleotides described herein may be increased. Alternatively, a strong promoter may be used to direct the expression of the polynucleotide. In another embodiment, the promoter, regulatory region and/or the ribosome binding site upstream of the gene can be altered to increase the expression. The expression may also be enhanced or increased by increasing the relative half-life of the messenger RNA. In another embodiment, the activity of the polypeptide itself may be increased by employing one or more mutations in the polypeptide amino acid sequence, which increase the activity. For example, altering the affinity of the polypeptide for its corresponding substrate may result in improved activity. Likewise, the relative half-life of the polypeptide may be increased. In either scenario, that being enhanced gene expression or increased activity, the improvement may be achieved by altering the composition of the cell culture media and/or methods used for culturing. "Enhanced expression" or "improved activity" as used herein means an increase of at least 5%, 10%, 25%, 50%, 75%, or even 100%, compared to a wild-type protein, polynucleotide, gene; or the activity and/or the concentration of the protein present before the polynucleotides or polypeptides are enhanced and/or improved. The activity of the GMS 08 protein may also be enhanced by contacting the protein with a specific or general enhancer of its activity.

Another aspect of the invention pertains to vectors, containing a nucleic acid encoding a protein according to the invention or a functional equivalent or portion thereof. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome.

Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., attenuator). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, encoded by nucleic acids as described herein, including, but not limited to, mutant proteins, fragments thereof, variants or functional equivalents thereof, and fusion proteins, encoded by a nucleic acid as described herein, e.g., GMS 08 proteins, mutant forms of GMS 08 proteins, fusion proteins and the like.

The recombinant expression vectors of the invention may be designed for expression of GMS 08 proteins in a suitable microorganism. For example, a protein according to the invention may be expressed in bacterial cells such as strains belonging to the genera *Gluconobacter, Gluconacetobacter* or *Acetobacter*. Expression vectors useful in the present invention include chromosomal-, episomal- and virus-derived vectors e.g., vectors derived from bacterial plasmids, bacteriophage, and vectors derived from combinations thereof, such as those derived from plasmid and bacteriophage genetic elements, such as cosmids and phagemids.

The DNA insert may be operatively linked to an appropriate promoter, which may be either a constitutive or inducible promoter. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Vector DNA may be introduced into suitable host cells via conventional transformation or transfection techniques. As used herein, the terms "transformation", "transconjugation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells may be found in Sambrook, et al. (supra), Davis et al., Basic Methods in Molecular Biology (1986) and other laboratory manuals.

In order to identify and select cells which have integrated the foreign DNA into their genome, a gene that encodes a selectable marker (e.g., resistance to antibiotics) is generally introduced into the host cells along with the gene of interest. Preferred selectable markers include those that confer resistance to drugs, such as kanamycin, tetracycline, ampicillin and streptomycin. A nucleic acid encoding a selectable marker is preferably introduced into a host cell on the same vector as that encoding a protein according to the invention or can be introduced on a separate vector such as, for example, a suicide vector, which cannot replicate in the host cells. Cells stably transfected with the introduced nucleic acid can be identified by drug selection (e.g., cells that have incorporated the selectable marker gene will survive, while the other cells die).

The invention provides also an isolated polypeptide having the amino acid sequence shown in SEQ ID NO:2 or an amino acid sequence obtainable by expressing a polynucleotide of the present invention, such as for instance a polynucleotide sequence shown in SEQ ID NO:1 in an appropriate host.

Polypeptides according to the invention may contain only conservative substitutions of one or more amino acids in the amino acid sequence represented by SEQ ID NO:2 or substitutions, insertions or deletions of non-essential amino acids. Accordingly, a non-essential amino acid is a residue that may be altered in the amino acid sequences shown in SEQ ID NO:2 without substantially altering the biological function. For example, amino acid residues that are conserved among the proteins of the present invention, are predicted to be particularly unamenable to alteration. Furthermore, amino acids conserved among the proteins according to the present invention and other GMS 08 proteins are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As mentioned above, the polynucleotides of the invention may be utilized in the genetic engineering of a suitable host cell to make it better and more efficient in the bioconversion of a carbon source such as e.g. glucose to biomass, i.e. reduction of carbon source diversion throughout the bioconversion process.

According to the invention a genetically engineered/recombinant host cell (also referred to as recombinant cell or transformed cell) may be produced carrying such a modified polynucleotide wherein the function of the linked protein is significantly modified in comparison to a wild-type cell such that the yield and/or productivity of biomass from a carbon source such as e.g. glucose is improved. The host cell may be selected from a microorganism capable of converting a given carbon source such as e.g. glucose into biomass, in particular *Gluconobacter oxydans*, preferably *G. oxydans* DSM 17078.

A "transformed cell" or "recombinant cell" is a cell into which (or into an ancestor of which) has been introduced, by means of recombinant DNA techniques, a nucleic acid according to the invention, or wherein the activity of the GMS 08 protein has been increased and/or enhanced. Suitable host cells include cells of microorganisms capable of converting a given carbon source such as e.g. glucose into biomass. In particular, these include strains from the genera *Pseudomonas, Pantoea, Escherichia, Corynebacterium, Ketogulonicigenium* and acetic acid bacteria like e.g., *Gluconobacter, Acetobacter* or *Gluconacetobacter*, preferably *Acetobacter* sp., *Acetobacter aceti, Gluconobacter frateurii, Gluconobacter cerinus, Gluconobacter thailandicus, Gluconobacter oxydans*, more preferably *G. oxydans*, most preferably *G. oxydans* DSM 17078.

Improved gene expression may also be achieved by modifying the GMS 08 gene, e.g., by introducing one or more mutations into the GMS 08 gene wherein said modification leads to a GMS 08 protein with a function which is significantly improved in comparison to the wild-type protein.

Therefore, in one other embodiment, the polynucleotide carrying the at least one mutation is derived from a polynucleotide as represented by SEQ ID NO:1 or equivalents thereof.

A mutation as used herein may be any mutation leading to a more functional or more stable polypeptide, e.g. more functional or more stable GMS 08 gene products. This may include for instance an alteration in the genome of a microorganism, which improves the synthesis of GMS 08 or leads to the expression of a GMS 08 protein with an altered amino acid sequence whose function compared with the wild type counterpart having a non-altered amino acid sequence is improved and/or enhanced. The improvement may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations.

An alteration in the genome of the microorganism leading to a more functional polypeptide may also be obtained by randomly mutagenizing the genome of the microorganism using e.g. chemical mutagens, radiation or transposons and selecting or screening for mutants which are better or more efficient producers of biomass. Standard methods for screening and selection are known to the skilled person.

In a specific embodiment, it is desired to knockout or suppress a repressor of the GMS 08 gene of the present invention, i.e., wherein its repressor gene expression is artificially suppressed in order to improve the yield and/or efficiency of biomass production when introduced into a suitable host cell. Methods of providing knockouts as well as microorganisms carrying such suppressed genes are well known in the art. The suppression of the repressor gene may be induced by deleting at least a part of the repressor gene or the regulatory region thereof. As used herein, "suppression of the gene expression" includes complete and partial suppression, as well as suppression under specific conditions and also suppression of the expression of either one of the two alleles.

The aforementioned mutagenesis strategies for GMS 08 proteins may result in increased yield and/or production of biomass. This list is not meant to be limiting; variations on these mutagenesis strategies will be readily apparent to one of ordinary skill in the art. By these mechanisms, the nucleic acid and protein molecules of the invention may be utilized to generate microorganisms such as *Gluconobacter oxydans* or related strains of bacteria expressing mutated GMS 08 nucleic acid and protein molecules such that the yield, efficiency and/or productivity of biomass production from a carbon source such as e.g. glucose is improved.

Biomass concentration can be measured using several methods known to the person skilled in the art, such as e.g. measuring the optical density of the respective cell suspensions at for instance a wavelength of 600 nm ($OD_{600}$), or measuring either the wet- or dry-cell mass concentration or by counting the numbers of cells of the respective cell suspension. Such methods of measurement are known in the art. Thus, the cell dry weight (CDW) [g/l] may be for instance measured on a dried and tared nitrocellulose filter with a pore size of e.g. 0.45 µm on which the culture broth is filtrated. After washing the filter with water, the weight of the dried filter is again determined and the CDW calculated as follows:

$$CDW = m(\text{dried filter after broth filtration}) - m(\text{dried filter before broth filtration})$$

In one aspect of the invention, microorganisms (in particular from the genera of *Gluconobacter, Gluconacetobacter* and *Acetobacter*) are provided that are able to perform such improved bioconversion. When measured by a method as described herein these organisms were found to have an improved capability to produce biomass from a carbon source such as e.g. glucose. Such may be achieved by increasing the activity of a GMS polypeptide, preferably a GMS 08 polypeptide. The yield of biomass produced from a carbon source, such as for instance glucose, when measured according to this method after an incubation period of 24 hours may be about 0.1 g or more dry biomass/g carbon source, preferably about 0.2 g or more dry biomass/g carbon source, or even about 0.3 g or more dry biomass/g carbon source, such as for instance about 0.4 g, 0.5 g, 0.6 g, 0.7 g, 0.8 g or 1.0 g or more dry biomass/g carbon source. Preferably, the carbon source is glucose.

The recombinant microorganism carrying e.g. a modified GMS 08 gene and which is able to produce biomass from a carbon source such as e.g. glucose in significantly higher yield, productivity, and/or efficiency may be cultured in an aqueous medium supplemented with appropriate nutrients under aerobic conditions. The cultivation may be conducted in batch, fed-batch, semi-continuous or continuous mode. The cultivation period may vary depending on for instance the host, pH, temperature and nutrient medium to be used, and is preferably about 1 to about 10 days when run in batch or fed-batch mode. The cultivation may be conducted at for instance a pH of about 4.0 to about 9.0, preferably about 5.0 to about 8.0. The preferred temperature range for carrying out the cultivation is from about 13° C. to about 36° C., preferably from about 18° C. to about 33° C. Usually, the culture medium may contain besides e.g. D-glucose as main carbon source other assimilable carbon sources, e.g., glycerol, D-mannitol, D-sorbitol, L-sorbose, erythritol, ribitol, xylitol, arabitol, inositol, dulcitol, D-ribose, D-fructose, sucrose and ethanol, preferably D-sorbitol, D-mannitol, D-fructose, glycerol and ethanol; and digestible nitrogen sources such as organic substances, e.g., peptone, yeast extract, baker's yeast, urea, amino acids, and corn steep liquor. Various inorganic substances may also be used as nitrogen sources, e.g., nitrates and ammonium salts. Furthermore, the culture medium usually may contain inorganic salts, e.g., magnesium sulfate, manganese sulfate, potassium phosphate, and calcium carbonate.

The nucleic acid molecules, polypeptides, vectors, primers, and recombinant microorganisms described herein may be used in one or more of the following methods: identification of *Gluconobacter oxydans* and related organisms; mapping of genomes of organisms related to *Gluconobacter oxydans*; identification and localization of *Gluconobacter oxydans* sequences of interest; evolutionary studies; determination of GMS 08 protein regions required for function; modulation of a GMS 08 protein activity or function; modulation of the activity of a GMS pathway; and modulation of cellular production of biomass from a carbon source such as e.g. glucose.

The invention provides methods for screening molecules which modulate the activity of a GMS 08 protein, either by interacting with the protein itself or a substrate or binding partner of the GMS 08 protein, or by modulating the transcription or translation of a GMS 08 nucleic acid molecule of the invention. In such methods, a microorganism expressing one or more GMS 08 proteins of the invention is contacted with one or more test compounds, and the effect of each test compound on the activity or level of expression of the GMS 08 protein is assessed.

The biological, enzymatic or other activity of GMS proteins can be measured by methods well known to a skilled person, such as, for example, by incubating a cell fraction containing the GMS 08 protein in the presence of its substrate, electron acceptor(s) or donor(s) including phenazine methosulfate (PMS), dichlorophenol-indophenol (DCIP), NAD, NADH, NADP, NADPH, which consumption can be directly or indirectly measured by photometric, colorimetric or fluorimetric methods, and other inorganic components which might be relevant for the development of the activity. Thus, for example, the activity of membrane-bound D-glucose dehydrogenase can be measured in an assay where membrane fractions containing this enzyme are incubated in the presence of phosphate buffer at pH 6, D-glucose and the artificial electron acceptors DCIP and PMS. The rate of consumption of DCIP can be measured at 600 nm, and is directly proportional to the D-glucose dehydrogenase activity present in the membrane fraction.

Furthermore, the activity of gluconokinase can be measured in an assay where soluble fractions containing this enzyme are incubated in the presence of glycylclycine buffer at pH 8, ATP, D-gluconic acid, MgCl2, NADP+, 6-phophsgluconate dehydrogenase. The change of the absorbance of reduced NADP can be measured at 340 nm (see also Izu et al., Purification and characterization of the *Escherichia coli* thermoresistant glucokinase encoded by the gntK gene, FEBS Lett. 1996 Sep. 23; 394(1):14-6.)

Thus, the present invention is directed to the use of a polynucleotide, polypeptide, vector, primer and recombinant microorganism as described herein in the production of biomass, i.e., the bioconversion of a carbon source such as e.g. glucose into biomass. In a preferred embodiment, a modified polynucleotide, polypeptide, vector and recombinant microorganism as described herein is used for improving the yield, productivity, and/or efficiency of said biomass production.

The terms "production" or "productivity" are art-recognized and include the amount of biomass formed within a given time and a given cultivation volume (e.g., kg product per hour per liter) from a given amount or concentration of a carbon source such as e.g. glucose. The term "efficiency of production" includes the time required for a particular level of production to be achieved (for example, how long it takes for the cell to attain a particular rate of output of a product). The term "yield" is art-recognized and includes the efficiency of the conversion of the carbon source into biomass. This is generally written as, for example, kg biomass per kg carbon source. By "increasing the yield and/or production of biomass" it is meant that in a given amount of culture over a given amount of time the biomass is increased. By measuring the increase in biomass- and decrease in carbon source concentration in a growing culture, one can calculate the yield of biomass on consumed carbon source; i.e. the weight of biomass obtained by bioconverting a determined weight of carbon source such as e.g. glucose, defined as kg biomass per kg carbon source consumed. To determine the consumption of carbon source, the residual amount of carbon source in the growth medium can be measured by methods well known in the art (e.g. HPLC). The increase of biomass can be measured by methods well known in the art (e.g. optical density at 600 nm, or measurement of dry weight of a sample).

The terms "biosynthesis" or a "biosynthetic pathway" are art-recognized and include the synthesis of a compound/product, preferably an organic compound, by a cell from intermediate compounds in what may be a multistep and highly regulated process. The term "bioconversion" is art-recognized and includes the conversion of a carbon source such as e.g. glucose into a product, i.e. biomass, by means of one or more biosynthetic step(s) which involve one or more enzyme(s) and/or transporter(s). The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The language "transport" or "import" is art-recognized and includes the facilitated movement of one or more molecules across a cellular membrane through which the molecule would otherwise either be unable to pass or be passed inefficiently.

In one preferred embodiment, the present invention is related to a process for the production of biomass from a carbon source such as e.g. glucose wherein a modified polynucleotide sequence as described above is introduced into a suitable microorganism and the recombinant microorganism is cultured under conditions that allow the production of biomass in high productivity, yield, and/or efficiency.

Recombinant microorganisms according to the present invention carrying e.g. a modified GMS gene, in particular a modified GMS 08 gene, and which are able to produce biomass from a carbon source such as e.g. glucose in significantly higher yield, productivity, and/or efficiency may advantageously be used in a number of applications. One particularly suited application is a method for the production of Vitamin C and/or intermediates thereof such like 2-keto-L-gulonic acid (2-KGA).

Thus, it is an aspect of the present invention to provide a process for the production of Vitamin C and/or 2-KGA wherein a nucleotide according to the invention or a modified polynucleotide sequence as described above is introduced into a suitable microorganism as described above wherein a suitable carbon source such as e.g. glucose is efficiently converted into biomass, the recombinant microorganism is cultured under conditions that allow the production of Vitamin C and/or 2-KGA in high productivity, yield, and/or efficiency, the produced fermentation product is isolated from the culture medium and optionally further purified.

The carbon sources used for the production of (1) biomass and (2) Vitamin C and/or 2-KGA may be the same or may differ. In one preferred embodiment, the carbon source(s) used for the production of biomass is different from the carbon source(s) used for the direct production of Vitamin C and/or 2-KGA. These two different carbon sources may be used simultaneously or sequentially, wherein a first carbon source would be used for the production of biomass, and this biomass would then be used to convert a second carbon source into Vitamin C and/or 2-KGA.

A suitable carbon source that can be converted directly into Vitamin C and/or 2-KGA may be selected from the D-glucose or D-sorbitol metabolization pathway such as, for example, D-glucose, D-sorbitol, L-sorbose, L-sorbosone, D-gluconate, 2-keto-D-gluconate or 2,5-diketo-gluconate or mixtures thereof. Preferably, the substrate is selected from for instance D-glucose, D-sorbitol, L-sorbose, L-sorbosone or mixtures thereof, more preferably from D-glucose, D-sorbitol, L-sorbose or mixtures thereof, and most preferably from D-sorbitol, L-sorbose or mixtures thereof.

Vitamin C as used herein may be any chemical form of L-ascorbic acid found in aqueous solutions, such as for instance undissociated, in its free acid form or dissociated as an anion. The solubilized salt form of L-ascorbic acid may be characterized as the anion in the presence of any kind of cations usually found in fermentation supernatants, such as for instance potassium, sodium, ammonium, or calcium. Also included may be isolated crystals of the free acid form of L-ascorbic acid. On the other hand, isolated crystals of a salt form of L-ascorbic acid are called by their corresponding salt name, i.e. sodium ascorbate, potassium ascorbate, calcium ascorbate and the like.

Conversion of a suitable carbon source into Vitamin C and/or 2-KGA in connection with the above process using a microorganism means that the conversion of the carbon source resulting in Vitamin C and/or 2-KGA is performed by the microorganism, i.e. the carbon source may be directly converted into Vitamin C and/or 2-KGA. Said microorganism is cultured under conditions which allow such conversion from said carbon source as it is known for the skilled person.

A medium as used herein for the above process using a microorganism may be any suitable medium for the production of Vitamin C and/or 2-KGA. Typically, the medium is an aqueous medium comprising for instance salts, substrate(s), and a certain pH.

The term "direct conversion" and the like is intended to mean that a microorganism is capable of the conversion of a certain carbon source into the specified product by means of one or more biological conversion steps, without the need of any additional chemical conversion step. For instance, the term "direct conversion of D-sorbitol into Vitamin C" is intended to describe a process wherein a microorganism is producing Vitamin C and wherein D-sorbitol is offered as a carbon source without the need of an intermediate chemical conversion step. A single microorganism capable of directly fermenting Vitamin C is preferred.

This invention is further illustrated by the following examples which should not be construed as limiting. The contents of all references, patent applications, patents and published patent applications, cited throughout this application are hereby incorporated by reference.

EXAMPLES

Example 1

Analytical Methods for Biomass and Glucose Determination

For determination of biomass production, cells of *G. oxydans* were grown at 27° C. for 3 days on MB agar, containing 25 g/l mannitol, 5.0 g/l yeast extract (Difco), 3.0 g/l Bactopeptone (Difco) and 15 g/l agar. Cells were resuspended in 10% glycerol (10 ml per plate) and 1 ml aliquots were stored at −80° C.

A baffled 500 ml shake flask with 100 ml medium No. 5 containing 50 g/l D-glucose, 0.5 g/l glycerol, 15 g/l yeast extract (Difco), 2.5 g/l MgSO$_4$.7H$_2$O, 0.3 g/l KH$_2$PO$_4$, 15 g/l CaCO$_3$ and 1 drop antifoam was inoculated with a 1 ml aliquot and incubated at 30° C. and 180 rpm in a shaker for 48 h. The optical density at 600 nm (OD$_{600}$) was determined using a Spectronic 400I/N spectrophotometer and an identical medium No. 5 flask was then inoculated with this culture, such that the start OD$_{600}$ in the second flask was 0.25. This flask was then further incubated at 30° C., 180 rpm for another 80 h with samples of 3 ml taken every 12 h for analysis of biomass and glucose concentrations as follows:

Production of biomass was determined via measurement of the dry weight of the sample. Reaction tubes were pre-dried at 40° C. under vacuum for 48 h and the weight of the empty tubes measured [w1]. The sample was added and the weight of the full tube determined [w2]. 0.1 ml 18.5% HCl was added to dissolve the CaCO$_3$. The tubes were subsequently centrifuged for 3 min at 13000 rpm. The supernatant was discarded, 0.5 ml of water was added and the pellet was resuspended. The tube was centrifuged again for 3 min at 13000 rpm and the supernatant was discarded. The pellet was dried at 40° C. under vacuum for 48 h and the tube containing the pellet again weighted [w3]. The concentration of biomass [B] in the sample was calculated as follows:

$$(w3-w1)/(w2-w1) \times 1000 = \text{concentration of biomass [g/kg]}$$

The amount or concentration of glucose [G] was measured by HPLC on an Hewlett-Packard 1100 instrument using an Aminex-HPX-78H (300×7.8 mm) column (Biorad, Reinach, Switzerland) combined with a LiChrospher-100—RP18, 5 µm precolumn (Merck, Darmstadt, Germany). The mobile phase was 0.004 M sulfuric acid, pumped at a flow rate of 0.6 ml/min. A refractive index detector was used to monitor the signal. External standard calibration was applied based on peak areas.

The yield, i.e. the amount of biomass (dry weight) obtained from conversion of D-glucose [g biomass/g D-glucose] after a given time was calculated as follows, wherein (t1) defines the concentration of biomass and D-glucose, respectively, measured during or at the end of cultivation, for instance after 24 or 48 h, and (t0) defines the respective concentrations at the beginning of the cultivation (see above):

$$[B(t1)-B(t0)]/[G(t1)-G(t0)] = \text{yield of biomass on consumed glucose [g/g]}$$

The volumetric biomass productivity [g/kg/h], i.e. the amount of biomass produced per liter of culture and per time unit was calculated as follows:

$$[B(t1)-B(t0)]/(t0-t1) = \text{volumetric biomass productivity [g/kg/h]}$$

Example 2

Preparation of Chromosomal DNA and Amplification of DNA Fragment by PCR

Chromosomal DNA of *Gluconobacter oxydans* DSM 17078 was prepared from the cells cultivated at 30° C. for 1 day in mannitol broth (MB) liquid medium consisting of 25 g/l mannitol, 5 g/l of yeast extract (Difco), and 3 g/l of Bactopeptone (Difco) by the method described by Sambrook et al (1989) "Molecular Cloning: A Laboratory Manual/Second Edition", Cold Spring Harbor Laboratory Press).

A DNA fragment was prepared by PCR with the chromosomal DNA prepared above and a set of primers, Pf (SEQ ID NO:3) and Pr (SEQ ID NO:4). For the reaction, the Expand High Fidelity PCR kit (Roche Diagnostics) and 10 ng of the chromosomal DNA was used in total volume of 100 µl according to the supplier's instruction to have the PCR product containing GMS 08 DNA sequence (SEQ ID NO:1). The PCR product was recovered from the reaction and its correct sequence confirmed.

Example 3

Overexpression of the GMS 08 Gene in *G. oxydans* DSM 17078-ΔGMS 01

*G. oxydans* DSM 17078-ΔGMS 01 was obtained by gene disruption using the sacB selection system (Link et al., J. Bacteriol., 179(20):6228-37, 1997; Schafer et al., Gene 22; 145(1):69-73, 1994). For this, a PCR product with an in-frame deleted GMS 01 gene was constructed by long-flanking homology PCR using genomic DNA obtained in Example 2 as template. The 5'-portion of the GMS 01 gene was amplified by PCR using primers coPCR-gdh-5F (SEQ ID NO:7) and coPCR-gdh-5R (SEQ ID NO:8), yielding PCR product A. The 3'-portion of the GMS 01 gene was amplified by PCR using primers coPCR-gdh-3F (SEQ ID NO:9) and coPCR-gdh-3R (SEQ ID NO:10), yielding PCR product B. In a third PCR reaction, a PCR product containing the in-frame deleted GMS 01 gene (SEQ ID NO:11) was obtained, using a 1:1 molar mixture of the PCR products A and B as template and coPCR-gdh-5F (SEQ ID NO:7) and coPCR-gdh-3R (SEQ ID NO:10) as primers.

The resulting PCR product containing the in-frame deleted GMS 01 gene was digested with PstI and HindIII and cloned into PstI-HindIII-digested pK19mobsacB vector, resulting in the deletion plasmid pK19mobsacB-ΔGMS 01. This plasmid was transformed into *G. oxydans* DSM 17078 selecting for transformants on media containing kanamycin. The integration of plasmid pK19mobsacB-ΔGMS 01 was confirmed by PCR analysis. To induce recombination of the integrated plasmid and replacement of the wild-type GMS 01 gene by the in-frame deleted GMS 01 gene, kanamycin-resistance colonies were plated onto media containing 10% sucrose without antibiotics. After several days, sucrose-resistant colonies appeared which were checked for kanamycin sensitivity and the replacement of the wild-type GMS 01 gene by the in-frame deleted GMS 01 gene by PCR analysis. One such mutant was found and named *G. oxydans* DSM 17078-ΔGMS 01.

For overexpression of GMS 08, the PCR product obtained in Example 2 was amplified using the primers gkGoxBglII_R (SEQ ID NO:5) and gkGoxXhoI_F (SEQ ID NO:6) and cloned into the expression vector pBBR1MCS2 (Kovach et al., "pBBRIMCS: a broad-host-range cloning vector", Biotechniques, 1994 May; 16(5):800-2; and Kovach et al., "Four new derivatives of the broad-host-range cloning vector pBBR1MCS, carrying different antibiotic-resistance cassettes", Gene, 1995 Dec. 1; 166(1): 175-6), containing a kanamycin resistance cassette, resulting in pBBR1MCS2-GMS 08. The gene was subcloned from pBBR1MCS2-GMS 08 into pBBR1MCS4 (Kovach et al., 1994 and 1995), which contains an ampicillin resistance cassette, by digesting pBBR1MCS2-GMS 08 with the restriction endonucleases SacI and KpnI to excise the GMS 08 gene. The gene was cloned into SacI-KpnI-digested pBBR1MCS4 to give plasmid pBBR1MCS4-GMS 08. The plasmid pBBR1MCS4-GMS 08 was used to transform *G. oxydans* DSM 17078-ΔGMS 01 to obtain a strain which overexpresses GMS 08 gene and in addition is disrupted in the GMS 01 gene. The strain was named *G. oxydans* DSM 17078-ΔGMS 01/pBBR1MCS4-GMS 08. Using an enzymatic assay the overexpression of GMS 08 in the background of *G. oxydans* DSM 17078-ΔGMS 01 was confirmed.

Example 4

Production of Biomass from D-Glucose in Liquid Cultures

Cells of *G. oxydans* DSM 17078-ΔGMS 01 and *G. oxydans* DSM 17078-ΔGMS 01/pBBR1MCS4-GMS 08 were cultivated as described above and the volumetric biomass productivity determined (see Example 1), wherein (t1)=71 h. The results are depicted in Table 1.

TABLE 1

Production of biomass from D-glucose

| Strain | Volumetric biomass productivity [g/kg/h] |
| --- | --- |
| DSM 17078-ΔGMS 01 | 0.035 |
| DSM 17078-ΔGMS 01/ pBBR1MCS4-GMS 08 | 0.054 |

Example 5

Presence of the GMS 08 Gene and Equivalents in Other Organisms

The presence of SEQ ID NO:1 and/or equivalents in other organisms than the ones disclosed herein before, e.g. organisms as mentioned in Table 2, may be determined by a simple DNA hybridization experiment.

Strains of *Acetobacter aceti* subsp. *xylinum* IFO 13693 and IFO 13773 are grown at 27° C. for 3 days on No. 350 medium containing 5 g/l Bactopeptone (Difco), 5 g/l yeast extract (Difco), 5 g/l glucose, 5 g/l mannitol, 1 g/l MgSO$_4$.7H$_2$O, 5 ml/l ethanol, and 15 g/l agar. All other *Acetobacter*, *Gluconacetobacter* and all *Gluconobacter* strains are grown at 27° C. for 3 days on mannitol broth (MB) agar medium containing 25 μl mannitol, 5 g/l yeast extract (Difco), 3 g/l Bactopeptone (Difco), and 18 g/l agar (Difco). *E. coli* K-12 is grown on Luria Broth agar medium. The other strains are grown on medium recommended by the suppliers or according to methods known in the art. Genomic DNA is extracted as described by e.g. Sambrook et al., 1989, "Molecular Cloning: A Laboratory Manual/Second Edition", Cold Spring Harbor Laboratory Press) from a suitable organism as, e.g. mentioned in Table 2.

Genomic DNA preparations are digested with restriction enzymes such as EcoRI or HindIII, and 1 μg of the DNA fragments are separated by agarose gel electrophoresis (1% agarose). The gel is treated with 0.25 N HCl for 15 min and then 0.5 N NaOH for 30 min, and then blotted onto nitrocellulose or a nylon membrane with Vacuum Blotter Model 785 (BIO-RAD Laboratories AG, Switzerland) according to the instruction of the supplier. The resulting blot is then brought into contact/hybridized with a solution wherein the probe, such as e.g. a DNA fragment with SEQ ID NO:1 sequence or a DNA fragment containing the part or whole of the SEQ ID NO:1 sequence to detect positive DNA fragment(s) from a test organism. A DIG-labeled probe, e.g. SEQ ID NO:1, may be prepared according to Example 1 by using the PCR-DIG labeling kit (Roche Diagnostics) and a set of primers, SEQ ID NO:3 and SEQ ID NO:4. A result of such a blot is depicted in Table 2.

The hybridization may be performed under stringent or highly stringent conditions. A preferred, non-limiting example of such conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C. Highly stringent conditions include, for example, 2 h to 4 days incubation at 42° C. in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 min in 2×SSC and 0.1% SDS at room temperature and then washing twice for 15-30 min in 0.5×SSC and 0.1% SDS or 0.1×SSC and 0.1% SDS at 65-68° C. To detect DNA fragments with lower identity to the probe DNA, final washing steps can be done at lower temperatures such as 50-65° C. and for shorter washing time such as 1-15 min.

The genes corresponding to the positive signals within the respective organisms shown in Table 2 can be cloned by a PCR method well known in the art using genomic DNA of such an organism together with a suitable primer set, such as e.g. SEQ ID NO:3 and SEQ ID NO:4 under conditions as described in Example 1 or as follows: 5 to 100 ng of genomic DNA is used per reaction (total volume 50 μl). Expand High Fidelity PCR system (Roche Diagnostics) can be used with reaction conditions consisting of 94° C. for 2 min; 30 cycles of (i) denaturation step at 94° C. for 15 sec, (ii) annealing step at 60° C. for 30 sec, (iii) synthesis step at 72° C. for 0.5 to 5 min depending to the target DNA length (1 min/1 kb); extension at 72° C. for 7 min. Alternatively, one can perform a PCR with degenerate primers, which can be synthesized based on SEQ ID NO:2 or amino acid sequences as consensus sequences selected by aligning several amino acid sequences obtained by a sequence search program such as BLASTP (or BLASTX when nucleotide sequence is used as a "query sequence") to find proteins having a similarity to the protein of SEQ ID NO:2. For PCR using degenerate primers, temperature of the second annealing step (see above) can be lowered to 55° C., or even to 50-45° C. A result of such an experiment is shown in Table 2.

Samples of the PCR reactions are separated by agarose gel electrophoresis and the bands are visualized with a transilluminator after staining with e.g. ethidium bromide, isolated from the gel and the correct sequence is confirmed.

Consensus sequences mentioned above might be amino acid sequences belonging to certain categories of several protein domain/family databases such as PROSITE (database of protein families and domains), COGs (Cluster of Ortholog Groups), CDD (Conserved Domain Databases), pfam (large collection of multiple sequence alignments and hidden Markov models covering many common protein domains and families). Once one can select certain protein with identical/similar function to the protein of this invention from proteins containing domain or family of such databases, corresponding DNA encoding the protein can be amplified by PCR using the protein sequence or its nucleotide sequence when it is available in public databases. Following organisms may further provide genes, which can be used as an alternative gene of this invention: *Rhodococcus* sp. RHA 1, *Bradyrhizobium japonicum* USDA 110, *Sinorhizobium meliloti* 1021, *Mesorhizobium loti* MAFF303099, *Burkholderia mallei* ATCC 23344, *Zymomonas mobilis* subsp. *mobilis* ZM4, and *Erwinia carotovora* subsp. *astrospetica* SCR11043.

Example 6

Overexpression of the GMS 08 Gene and Equivalents in other Organisms for Production of Biomass In order to improve biomass production in a suitable microorganism from a carbon source such as e.g. glucose, the GMS 08 gene and equivalents as e.g. a PCR product obtained in Example 6, referred to hereafter as gene X, can be used in an overexpression system according to Example 2 or can be cloned into pCR2.1-TOPO (Invitrogen, Carlsbad, Calif., USA) and used to transform *E. coli* TG1 to have a Ap$^r$ transformant carrying pCR2.1-TOPO-gene X, i.e. carrying a PCR product obtained in Example 4. The insert is amplified with a set of primers, PfNdeI [SEQ ID NO:3 with CCCAT at the 5'-end] and PrHindIII [SEQ ID NO:4 with CCAAGCTT at the 5'-end], by PCR. Resulting PCR product is digested with NdeI and HindIII and the fragment is inserted together with PcrtE-SD (Shine-Dalgarno) fragment (WO 02/099095) digested with XhoI and NdeI into pVK100 (ATCC 37156) between the sites of XhoI and HindIII. *E. coli* TG1 is transformed with the ligation product to have Tc$^r$ transformant carrying plasmid pVK-PcrtE-SD-gene X, which is then used to transform a suitable host, e.g. *G. oxydans* DSM 17078 by electroporation to have e.g. Tc$^r$ *G. oxydans* DSM 17078/pVK-PcrtE-SD-gene X.

Further modifications including genes involved in the conversion of a carbon source such as e.g. glucose into biomass within said strains may be generated to improve biomass production within such strains.

Production of biomass from a carbon source such as e.g. glucose using the cells of the recombinant cells of e.g. *G. oxydans* strains DSM 17078 and the corresponding wild-type strain are performed according to according to Example 4.

In a reaction with 5% glucose as carbon source, the mutant strain *G. oxydans* DSM 17078-ΔGMS 01/pBBRIMCS4-GMS 08 can produce at least more than 150% biomass compared to the strain *G. oxydans* DSM 17078-ΔGMS 01.

TABLE 2

Equivalents of the GMS 08 gene in other organisms.

| Strain | Signal 1 | Signal 2 | Signal 3 |
|---|---|---|---|
| *G. oxydans* DSM 17078 | ++++ | + | + |
| *G. oxydans* IFO 3293 | ++++ | + | + |
| *G. oxydans* IFO 3292 | ++++ | + | + |
| *G. oxydans* ATCC 621H | ++++ | + | + |
| *G. oxydans* IFO 12528 | ++++ | + | + |
| *G. oxydans* G 624 | ++++ | + | + |
| *G. oxydans* T-100 | ++++ | + | + |
| *G. oxydans* IFO 3291 | ++++ | + | + |
| *G. oxydans* IFO 3255 | ++++ | + | + |
| *G. oxydans* ATCC 9937 | ++++ | + | + |
| *G. oxydans* IFO 3244 | ++++ | + | + |
| *G. cerinus* IFO 3266 | ++++ | + | + |
| *G. frateurii* IFO 3260 | ++++ | + | + |
| *G. oxydans* IFO 3287 | ++++ | + | + |
| *Acetobacter aceti* subsp. *orleanus* IFO 3259 | ++ | − | + |
| *Acetobacter aceti* subsp. *xylinum* IFO 13693 | ++ | − | + |
| *Acetobacter aceti* subsp. *xylinum* IFO 13773 | ++ | − | + |
| *Acetobacter* sp. ATCC 15164 | ++ | − | + |
| *G. thailandicus* NBRC 100600 | ++ | + | + |
| *Gluconacetobacter liquefaciens* ATCC 14835 | ++ | + | + |
| *Gluconacetobacter polyoxogenes* NBI 1028 | ++ | + | + |
| *Gluconacetobacter diazotrophicus* ATCC 49037 | ++ | + | + |
| *Gluconacetobacter europaeus* DSM 6160 | ++ | + | + |
| *Acetobacter aceti* 1023 | ++ | − | + |
| *Acetobacter pasteurianus* NCI 1193 | ++ | − | + |
| *Pseudomonas putida* ATCC 21812 | + | − | + |
| *Pseudomonas aeroginosa* PAO1 | + | − | + |
| *Pseudomonas fluorescens* DSM 50106 | + | − | + |
| *Pseudomonas syringae* B728a | + | − | + |
| *Rhodopseudomonas palustris* CGA009 | + | − | + |
| *Pantoea citrea* 1056R | + | − | + |
| *E. coli* | + | − | + |
| *Saccharomyces cerevisiae* | − | − | − |
| *Aspergillus niger* | − | − | − |
| Mouse | − | − | − |

Signal 1: Detection of DNA on a blot with genomic DNA of different strains and SEQ ID NO: 1 as labeled probe.
Signal 2: Detection of DNA of different strains in a PCR reaction using primer pair SEQ ID NO: 3 and SEQ ID NO: 4.
Signal 3: Detection of DNA of different strains in a PCR reaction using degenerate primers.
For more explanation refer to the text.

The invention claimed is:

1. A process for production of biomass from a carbon source, the process comprising cultivating a *Gluconobacter* microorganism in an aqueous nutrient medium under conditions that allow growth on said carbon source, said *Gluconobacter* microorganism being genetically engineered by disruption of a gene encoding a PQQ-dependent glucose dehydrogenase having at least 90% identity to the PQQ-dependent glucose dehydrogenase encoded by SEQ ID NO: 11 and introduction of a polynucleotide comprising a nucleotide sequence encoding a gluconate kinase, wherein the nucleotide sequence is selected from the group consisting of:
   (a) a nucleotide sequence encoding a polypeptide comprising SEQ ID NO:2;
   (b) a nucleotide sequence comprising SEQ ID NO:1;
   (c) a nucleotide sequence obtainable by polymerase chain reaction using genomic DNA from *Gluconobacter* as a template and the primer set according to SEQ ID NO:3 and SEQ ID NO:4 with an annealing step at 60° C. for 30 sec; and
   (d) a nucleotide sequence, selected from *Gluconobacter*, *Gluconacetobacter* or *Acetobacter*, the complementary strand of which hybridizes under highly stringent conditions to the nucleotide sequence as defined in (a), said highly stringent conditions comprising the steps of incubation of hybridization filters for 2 h to 4 days at 42° C. in a solution comprising 50% formamide followed by washing the filters twice for 5 to 15 minutes in 2×SSC/0.1% SDS at room temperature and twice for 5 to 30 minutes in 0.1×SSC/0.1% SDS at 65 to 68° C.;
   wherein a yield of at least 0.2 g biomass per gram glucose is produced.

2. A process for production of biomass from a carbon source, the process comprising cultivating a *Gluconobacter* microorganism genetically engineered by disruption of a gene encoding a PQQ-dependent glucose dehydrogenase having at least 90% identity to the PQQ-dependent glucose dehydrogenase encoded by SEQ ID NO: 11 and overexpressing an endogenous gene comprising a polynucleotide leading to
   an improved yield and/or production of biomass from a carbon source produced by said microorganism, wherein said nucleotide sequence encodes a gluconate kinase and is selected from the group consisting of:
   (a) a nucleotide sequence encoding a polypeptide comprising SEQ ID NO:2;
   (b) a nucleotide sequence comprising SEQ ID NO:1;
   (c) a nucleotide sequence obtainable by polymerase chain reaction using genomic DNA from *Gluconobacter* as a template and the primer set according to SEQ ID NO:3 and SEQ ID NO:4 with an annealing step at 60° C. for 30 sec; and
   (d) a nucleotide sequence, selected from *Gluconobacter*, *Gluconacetobacter* or *Acetobacter*, the complementary strand of which hybridizes under highly stringent conditions to the nucleotide sequence as defined in (a), said highly stringent conditions comprising the steps of incubation of hybridization filters for 2 h to 4 days at 42° C. in a solution comprising 50% formamide followed by washing the filters twice for 5 to 15 minutes in 2×SSC/0.1% SDS at room temperature and twice for 5 to 30 minutes in 0.1×SSC/0.1% SDS at 65 to 68° C.;
   wherein a yield of at least 0.2 g biomass per gram glucose is produced.

3. A process for production of biomass from a carbon source, the process comprising cultivating a *Gluconobacter* microorganism genetically engineered by disruption of a gene comprising the nucleotide sequence according to SEQ ID NO:11 and introduction of a polynucleotide comprising a nucleotide sequence encoding a gluconate kinase, wherein the nucleotide sequence is selected from the group consisting of:
   (a) a nucleotide sequence encoding a polypeptide comprising SEQ ID NO:2;
   (b) a nucleotide sequence comprising SEQ ID NO:1;
   (c) a nucleotide sequence obtainable by polymerase chain reaction using genomic DNA from *Gluconobacter* as a template and the primer set according to SEQ ID NO:3 and SEQ ID NO:4 with an annealing step at 60° C. for 30 sec; and
   (d) a nucleotide sequence, selected from *Gluconobacter*, *Gluconacetobacter* or *Acetobacter*, the complementary strand of which hybridizes under highly stringent conditions to the nucleotide sequence as defined in (a), said highly stringent conditions comprising the steps of incubation of hybridization filters for 2 h to 4 days at 42° C. in a solution comprising 50% formamide followed by washing the filters twice for 5 to 15 minutes in 2×SSC/0.1% SDS at room temperature and twice for 5 to 30 minutes in 0.1×SSC/0.1% SDS at 65 to 68° C.;
   wherein a yield of at least 0.2 g biomass per gram glucose is produced.

4. The process according to claim 3, wherein said polynucleotide sequence is present in the form of a vector.

5. The process according to claim 3, wherein said microorganism is genetically altered in such a way that it leads to an improved yield and/or efficiency of biomass produced from a carbon source by said microorganism.

6. The process according to claim 3 which is capable of producing biomass from glucose in a yield of at least about 0.2 g biomass/g glucose.

7. The process according to claim 6, wherein the yield is at least about 0.3 g biomass/g glucose.

8. The process according to claim 3, wherein the polynucleotide is operatively linked to expression control sequences and transferred into the microorganism.

9. The process according to claim 1, wherein the genetically engineered microorganism has increased and/or improved gluconate kinase activity compared to the non-genetically engineered microorganism.

10. The process according to claim 9, wherein the polynucleotide is overexpressed in the genetically engineered microorganism.

11. The process according to claim 1, wherein the carbon source is selected from the group consisting of glucose, sucrose, maltose, starch, cellulose, cellobiose, lactose, isomaltose, dextran, trehalose, and mixtures thereof.

12. The process according to claim 2, wherein the carbon source is selected from the group consisting of glucose, sucrose, maltose, starch, cellulose, cellobiose, lactose, isomaltose, dextran, trehalose, and mixtures thereof.

13. The process according to claim 3, wherein the carbon source is selected from the group consisting of glucose, sucrose, maltose, starch, cellulose, cellobiose, lactose, isomaltose, dextran, trehalose, and mixtures thereof.

14. The process according to claim 1, wherein the microorganism is selected from the group consisting of *Gluconobacter frateurii*, *Gluconobacter cerinus*, *Gluconobacter thailandicus*, and *Gluconobacter oxydans*.

15. The process according to claim 1, wherein the microorganism to be genetically engineered is *Gluconobacter oxydans* DSM 17078.

16. The process according to claim 2 which is capable of producing biomass from glucose in a yield of at least about 0.2 g biomass/g glucose.

* * * * *